(12) United States Patent
Kåhre

(10) Patent No.: US 8,760,640 B2
(45) Date of Patent: Jun. 24, 2014

(54) OPTICAL SYSTEM

(76) Inventor: Jan Kåhre, Helsinki (FI)

( * ) Notice: Subject to any disclaimer, the term of this patent is extended or adjusted under 35 U.S.C. 154(b) by 304 days.

(21) Appl. No.: 13/021,234

(22) Filed: Feb. 4, 2011

(65) Prior Publication Data

US 2011/0194109 A1    Aug. 11, 2011

(51) Int. Cl.
*G01N 21/41*    (2006.01)

(52) U.S. Cl.
USPC .......................................... 356/135; 356/128

(58) Field of Classification Search
USPC ................................................. 356/128, 135
See application file for complete search history.

(56) References Cited

U.S. PATENT DOCUMENTS

| | | | | |
|---|---|---|---|---|
| 4,306,805 | A * | 12/1981 | Arrington | 356/133 |
| 5,042,893 | A * | 8/1991 | Ong | 385/49 |
| 5,742,382 | A * | 4/1998 | K.ang.hre | 356/136 |
| 6,070,093 | A * | 5/2000 | Oosta et al. | 600/316 |
| 6,538,727 | B2 * | 3/2003 | Nicholas | 356/136 |
| 7,282,105 | B1 * | 10/2007 | Plunkett et al. | 156/154 |
| 2001/0035950 | A1 * | 11/2001 | Nicholas | 356/136 |
| 2005/0151975 | A1 * | 7/2005 | Melnyk | 356/480 |
| 2009/0279074 | A1 * | 11/2009 | Seaver | 356/73 |

FOREIGN PATENT DOCUMENTS

| | | |
|---|---|---|
| GB | 2460305 A | 12/2009 |
| WO | 2009/137122 A2 | 11/2009 |

OTHER PUBLICATIONS

Finland Patent Office, Search Report in FI20105110, Dec. 14, 2010.

* cited by examiner

*Primary Examiner* — Roy M Punnoose
(74) *Attorney, Agent, or Firm* — Piedmont Intellectual Property

(57) ABSTRACT

An optical instrument includes a controller and a field head arranged for measuring the refractive index of a medium, or a derivable quantity therefrom. The field head includes a measurement prism having a medium-boundary surface, a first wave guide for providing broad-band light from a broad band light source, a dispersive element for dispersing the broad-band light into at least one component light beam of plural component light beams, so that each incident component light beam has a differently directed propagation path and at least one different wave length, and a condenser for collecting at least one component light beam reflected at the medium-boundary surface into a second wave guide. The dispersive element is arranged to direct at least one component light beam into a critical angle of total reflection from the boundary surface, and at least other light beam component into an angle leading into the condenser arranged to collect at least one other component light beam to be passed to a spectrometer. The controller of a field head includes a light source for providing poly-chromatic light into a first wave guide for forming a plurality of component light beams to propagate in the field head and a spectrometer for spectrum analysis of light inputted via at least one input wave guide from the field head.

22 Claims, 2 Drawing Sheets

OPTICAL SYSTEM

This application claims priority from Finnish Patent Application No. 20105110 filed on Feb. 5, 2010, which is incorporated here by reference.

FIELD

The field of the invention belongs in a very general level to determination of properties of a medium, but more specifically by utilizing the optical properties of a medium and/or the utilization thereof for a derivable quantity determination, as indicated in the preamble of the independent claim.

BACKGROUND

Certain optical instruments can be used for measuring refractive index of a substance, or for determining a derivable quantity as based on its dependence on the refractive index. As an example of such a derivable quantity, the measurement of concentration of a component in a medium substance can be made as based on the refraction index measurement. Other derivable quantities comprise density, content of other substances, conductivity, etc. Such instruments utilizing the same principle may apply in suitable part also for other mediums than liquids, i.e. one can determine refractive index also for measuring gases, liquids and transparent solid substances. Liquids can be oils, water-based liquids, solutions thereof etc. Solids can be glass, diamonds or translucent solids.

An ensemble of known measurement procedures are based on the Snell's law and utilization its predictions on the critical angle ($\alpha_c$) of total reflection from a boundary surface between two optically different media (refractive indexes $n_1$ and $n_2$). In such set-ups the boundary surface is formed by the window at the medium whose refractive index is about to be measured.

FIG. 1A illustrates a setup for determination of a refractive index of a medium as based on utilization of the Snell's law.

$$\sin(\alpha_c) = n_1/n_2 = n \quad (1)$$

The light source in FIG. 1A is illustrated by a LED. The light thereof is directed to the boundary surface between the medium S and the measurement prism P forming the window there between. In FIG. 1A the prism sides act as mirrors for bending the path of light rays, whose directions are illustrated by the arrows. The reflected rays of light (from the boundary) form an image ACB, where the C represents the position of the incoming rays at the corresponding critical angle to the detector. The rays arriving to part A are totally reflected from the boundary to the detector but the rays at the B are only partly reflected or scattered, but also partly refracted into the medium S. Thus, the position of the shadow edge C between the light area A and the dark area B indicate the value of the critical angle for total reflection and thus the refractive index can be calculated from the value used as estimate, to be used as such or for determination of a derivable quantity such as concentration component of the medium S if the medium were a liquid.

In such a measurement, when the component concentration in the medium S changes, also the place of the shadow edge changes consequently. In a case of a low concentration of the medium component with a refractive index, dependent on the concentration, the light area at A is larger than the area at B, and in the case of high concentrations vice versa. When the concentration changes, also the position of the C changes.

The shadow edge C can be detected by an imaging element such as CCD-element for instance. Such an optical instrument is disclosed in further detail at www.kpatents.com/pdf/downloads/pr-23.pdf.

Broad-band source for poly-chromatic light allows a continuous measurement of the refractive index. The wavelength of the reflection band edge is measured by noting the wavelengths where a sudden change in spectral intensity occurs and with the index of the prism sensor and the angle of incidence to the prism face known, the index of refraction of the substance is determined also from the Snell's law.

However, the intensity I of reflected light at a boundary surface between the two media is a function of wavelength $\lambda$ and incident angle $\alpha$, $$I = I(\lambda, \alpha, n), \quad (2)$$

where n is the relative index of refraction (i.e. $n_1/n_2$) defined by the two media at the boundary. The relative index n is a function of the temperature $n=n(T)$. In addition, dependencies may occur also from other, environmental quantities, but as they may be not significant, are not further considered here for simplicity reasons.

In known techniques applying polychromatic light, the dispersed intensity of the light from the boundary into the critical angle of the total reflection in the medium is to be measured with a constant $\alpha$, angle of incidence. Dispersion occurring at the boundary surface between the prism and the sample, i.e. is utilized as the measurement device measures the dispersion of the critical angle of total reflection in the medium to be measured.

In such known techniques, the measurement utilizes a single ray of polychromatic light with a constant incident angle. It is utilizing the effect, in which part of the spectrum has a total reflection, part has not. In the attached drawing FIG. 1B and in the table below (where $\alpha_c$ is the critical angle, angle of total reflection) we can see for the Blue-to-Red spectrum, that the shift of the critical angle $\alpha_c$ is of the order of 1 degree. If used for concentration measurement, with a typical full range 0%-100% concentration it corresponds to an angle of the order of 12 degrees, we can see that the maximum obtainable measuring range is limited to $\frac{1}{12}$ or +/−4% concentration. This may be sufficient for some applications, such as measurement of salinity in seawater, which naturally is characterized by small fluctuations. Such a narrow range is not sufficient for a wide spread utilizable industrial instrument. The dashed line illustrating the blue (B) wavelength is dashed, as in the illustrative example of FIG. 1B some blue light (B) is reflected partially, and partially refracted into the medium.

|  | $\lambda$ | $\alpha$ | |
| --- | --- | --- | --- |
|  | nm | 0% | 100% |
| Blue (B) | 486.1 | 50.369 | 62.283 |
| Yellow (Y) | 589.3 | 50.879 | 63.137 |
| Red (R) | 656.3 | 51.168 | 63.453 |

Thus, there is a need to simplify the structure of optical instrument as well as to gain simultaneously more versatile and durable instrument structure that does not need back-up as often as the known devices, but would have a sufficiently wide range applicability for the measurement. Especially there is a need for such a simple instrument for use in fire sensitive and/or explosive gases/vapors containing environments.

SUMMARY

As the above referred need and the required properties may be not present in a single device, such an optical instrument is presented in the embodied and claimed invention.

According to a first aspect of the invention, in embodiments of the invention, polychromatic light is used for providing broad band light to be used in the measurement of index of refraction and/or a derivable quantity, so that a related instrument uses a range of incident angles of the light where every angle is represented by a practically monochromatic light beam, a component light beam (CLB).

By using polychromatic light as dispersed, before its entry to the boundary surface between the media, for monochromatic light component beams each representing an incident angle of the light in the CLBs, embodiments have in fact advantage of having eliminated the influence of dispersive effect that the known techniques is utilizing (FIG. 1B). By this way the embodiments of the invention easily reach a full span of 0-100% concentration, in more quantifiable form for the spectrometer or an analyzer of a kind. This is desirable in an industrial instrument, provided also that as exactly the same instrument can be used for most, if not totally all, possible applications. Thus as a bonus, further only one kind of back-up instrument is necessary, and certain redundancy can be obtained for calibration and/or self-calibration purposes.

The aim to fulfill the above referred need is achieved by the embodied system that comprises the field head connectable to a controller and the controller of the field head, which as embodied needs no electrical energy supply due to the all-optical working principle. Thus such a field head is by itself classified as intrinsically safe for use in fire/explosion sensitive conditions. Together with the wide measurement range it makes a new unique combination to fulfill industrial measurement need.

According to the invention field head of an optical instrument for measuring refractive index of a medium, or a derivable quantity thereof, in contact with a measurement prism boundary surface of the field head, further comprises in the field head of the optical instrument:
  a first wave guide means for providing broad-band light from a broad band light source,
  dispersive element for dispersing the broad-band light into at least one component light beam belonging to a plurality of component light beams, so that each incident component light beam in the plurality has differently directed propagation path and at least one different wavelength distinctive from the same, of the other members in the plurality of component light beams,
  condenser for collecting, the at least one component light beam as reflected at the boundary surface of the measurement prism, into a second wave guide means,
wherein the dispersive element is arranged to direct at least one the component light beam into a critical angel of total reflection from the boundary surface, and at least another light beam component into an angle leading into the condenser arranged to collect at least one of the another component light beam to be passed to a spectrometer that is arranged to do spectrometer analysis for the reaching component light beams.

According to an embodiment of the invention, the field head is arranged so that a component light beam in the plurality of light beams is arranged to be incident to the boundary surface, and out of focus at the boundary surface. This way it is possible to extend the internal distance inside the field head longer from the incident source part to the collector and thus to have a wider range of the angles for the monochromatic component light beams, if the focused geometry is not enough for desired range from Blue to Red at the respective extremes of the cone of the broad band light as used.

According to an embodiment of the invention, the field head is arranged so that a component light beam in the plurality of light beams is arranged to be incident to the surface in a converging geometry to focus on the surface. So in some instrument applications the case can be advantageous with somewhat opposite geometry in suitable part to the above mentioned desires.

According to an embodiment of the invention, the field head is arranged so that a component light beam in the plurality of light beam is arranged to be dispersed into a component light beam specific incident angle as a function of wavelength of the broad band light.

According to an embodiment of the invention, the field head is arranged so that the field head comprises wave guide connectors for guiding light at least into the first wave guide means or out of the second wave guide means. This allows to situate the field head remotely to the controller and thus into a place where for example explosive gases may be not present and electricity can be used, on the contrary to the conditions near the field head.

According to an embodiment of the invention, the field head is arranged so that the functionality of at least one of the dispersive element and measurement prism is implemented by a diffractive grating. This may be advantageous for a lighter instrument, although gratings may be more expensive than mere prisms.

According to an embodiment of the invention, the field head is arranged so that a dispersive element and measurement prism are combined or are joined into the same component. So the packing density may be increased, where it is desirable more than the very wide span of angles from blue to red or vice versa.

According to an embodiment of the invention, the field head is arranged so that the field head comprises a wave guide line output for an optical compensation signal for a controller. This way the optical radiation can be sent for the spectrometer to see the intensities before the sensor prism.

According to an embodiment of the invention, the field head is arranged so that the field head comprises an antistatic coating to avoid charge build-up on the field head and/or grounding means to lead charge built-up to a grounding. According to an embodiment, it is possible so gain superior properties against the static electricity built up, useful advantage in explosive conditions. According to an embodiment, the sensing prism may be coated by or made of Indium-Tin-Oxide, (ITO), to maintain the electrical conductivity, although made by the expense of durability in certain processes. According to a variant of an embodiment, the wave guide means between the filed head and the controller are at least partly so coated on the exterior surface if not totally, so to make them connectable to the grounding.

According to an embodiment of the invention the field head is arranged so that the filed head comprises, in addition to the operative opto-mechanical infra structure for the lines and supports etc., only wave guide based control signal connectors for controlling the field head. This is advantage of related embodiments to avoid electric sparks in explosive conditions.

According to an embodiment of the invention, controller of a field head of an optical instrument, comprises:
  light source for providing light into an output via a first wave guide means for formation of a plurality of component light beams into a field head for the use therein, spectrometer for spectrum analysis of light inputted therein via at least one input wave guide from the field head. Additionally maintaining infrastructure for the power sources and mechanical structures for the assemblies, which may be made as described in the known techniques in suitable part.

According to an embodiment of the invention, the controller of the field head is arranged so that the light source is arranged to transmit polychromatic light with a continuous wave length distribution, so providing the component light beams for the range from red (R) to blue (B) (or the vice versa), or other broad band range as a sub range to the range. In a variant of an embodiment a broad band range can comprise parts outside the visible light wave length range, or can be situated optionally in whole to the ultraviolet range or to the infrared range.

According to an embodiment of the invention, the controller of the field head is arranged so that, the light source comprises a plurality of monochromatic light sources for providing the component light beams. This may be useful, if only few component light beams are to be used, for example of detecting mere certain thresholds.

According to an embodiment of the invention, the controller of the field head is arranged so that the light source is arranged to provide a compensation signal to the spectrometer for compensation of the light source characteristics. This embodiment is useful if the compensation is needed, but is not desired to route the signal via the field head, because of mechanical reasons relating to the space available for the route or other reason. However, sometimes for certain embodiments the inputting may be useful to implement via the mere field head or both ways.

According to an embodiment of the invention, the controller of the field head is arranged so that the light source comprises at least one light source that can produce light pulses. This way the controller can be kept cooler and the warm transfer via the optical line may be avoided to a suitable extent. According to an embodiment of the invention, in the controller head according to an embodiment of the invention, the light source comprises control means to alter the wave length of the light, continuously or in stepwise, control means to control wave length from one pulse to another, and/or means to vary pulse length versus pitch, or pulse frequency.

According to an embodiment of the invention, an optical system according to an embodiment of the invention comprises at least one field head and at least one controller.

According to a variant of the embodiment, a first ensemble of field heads can be used in combination of a second ensemble of controller units so that in the first and second ensemble there is at least one kind of the instrument of the species as embodied as described for the embodiments of the invention. Also several filed heads can be used in combination of a one controller, or vice versa. This is advantageous when the refraction index is expected to change in a process during the flow, when monitoring a process flow in several locations. In certain cases a redundant unit may be needed for securing a unit operation, for field head and/or its controller.

According to an embodiment of the invention, the optical system of the field head is arranged so that the field head and the controller are integrated into the same cover to form a device. Sometimes it is handy to have the both parts together, as for instance for lab use. This is advantageous if the same manufacturer's device in the process control were also utilizable in the lab for getting more correlated results. According to a variant of the embodiment the field head and the controller are arranged to be attachable to each other directly, or optionally via wave guides.

According to an embodiment of the invention a method of determining refractive index via total reflection of a component light beam belonging to a plurality of light beams of broad-band multi-wavelength light, from a filed head prism-measurable medium-boundary surface, comprises:
  directing at least one the component light beam at a first wave length to the boundary surface at a critical angle of total reflection,
  directing at least one another component light beam at a second wave length to the boundary surface to propagate on a path leading to a condenser,
  collecting by the condenser reflected light to the spectrometer that is arranged for spectrometric analysis of component light beams,
  detecting, based on the information on the wavelengths of sent at least one component light beam in a plurality of component light beams, a first missing component light beam from the spectrum,
  computing refractive index of the medium as based on the missing component's wave length.

According to an embodiment of the invention the optical system is configured to constitute a process-refractometer.

According to an embodiment of the invention, a software product on a computer readable medium, comprises software means arranged to control the spectrometer functionality according to the method according to an embodiment of the invention when the software means is executed and run in a computer. In accordance of the embodiment, the software can be arranged to control the light source properties, and the spectrometer, compensation and/or input/output data transfers as well as data analysis, setting thresholds, alarms, and/or communication facilities built in the system for the communication of the data to the controller and/or from the controller, wirelessly and/or via cable.

According to an embodiment of the invention, a software product, the software product comprises at least one of the following; spectrometer controlling means, spectrum scanning and/or analyzing means, shoulder defining means, datalogging means, statistical analysis means, data-base means for storing and/or handling of the measurement data and graphical means arranged to provide illustrations on the measurement results onto a display means for displaying data.

The spectrometer as such can be implemented in many ways known to a skilled man in the art as such. Although the scope of the embodiments is not directed to mere known spectrometer implementation as such, according to an embodiment of the invention, the spectrometer in the embodied optical system can be implemented by using such a plurality of photo-cells that comprises at least one photo-cell, so arranged that at least one of the photo cells in the plurality is arranged to detect changes in the component light beam (CLB), so that the output quantity of the photo-cell's detector circuitry is arranged to change as a response to the detected change of the CLB as an initiative for the response.

According to an embodiment of the invention the spectrometer can be implemented so that it comprises a CCD-element comprising pixels as arranged for the spectrometer operation for the CCD in whole.

According to an embodiment of the invention the spectrometer comprises at least one photo-cell for each CLB, so quantizing the CLB's. According to a variant of such an embodiment, an ensemble of CCD-element's/cell's pixels are arranged for each CLB. The quantization can be implemented in an ensemble of embodiments in a spatial way, i.e. for example by arranging the photo-cells in to a geometry of plain linear straight line, or into a line but curved segment of a circle to receive the CLBs. Such a line comprises minimum normal-to-line-dimension of at least one photo-cell unit. In an embodiment also redundant photo-cells can be used for better statics, if so available in the particular embodiment. The quantization can be optionally implemented in an ensemble of embodiments in a temporal way. In a temporal quantization the CLBs may be not present simultaneously, but are introduced to the field head in a periodical or in an intermittent sequence.

According to an embodiment of invention, the condensing can be made in suitable part by directing the CLBs into an optical fiber bunch arranged so to quantize the CLBs into the corresponding optical fibers for the delivery to the spectrometer and thus for the analysis. In such an embodiment, also a compensation signal can be, but is not necessarily, delivered to the spectrometer.

Figure 1A:
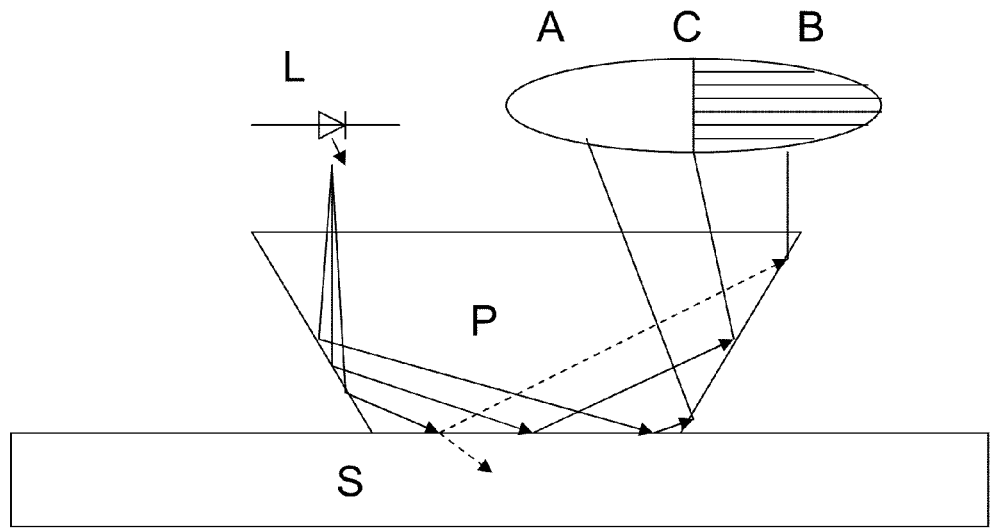
FIG. 1A, 1B Show schematic illustrations on known techniques.
Figure 1B:
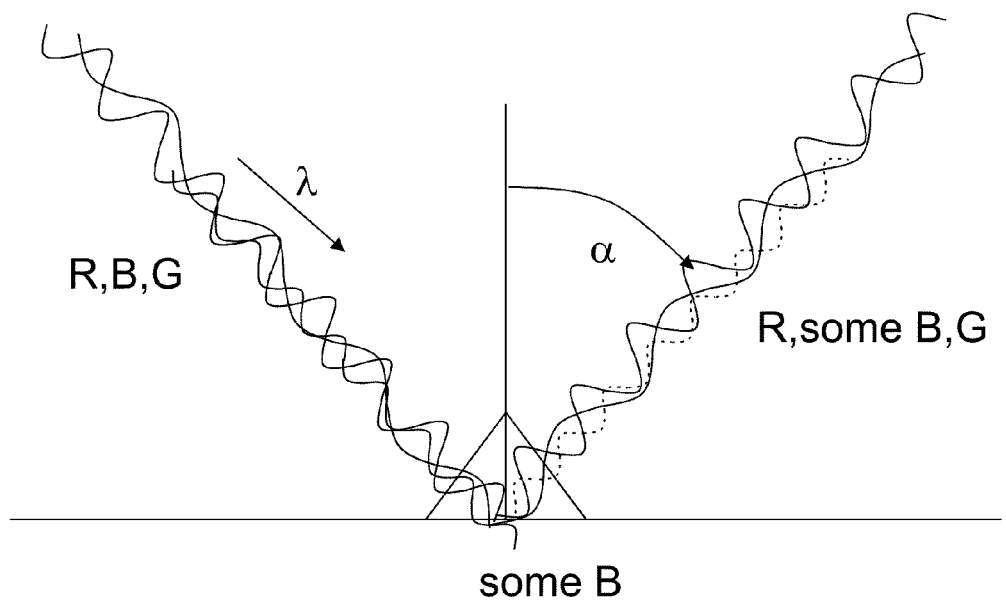

As FIGS. 1A and 1B has been used for illustrating known techniques, in the following FIG. 2-FIG. 3. illustrate an ensemble of examples on the embodiments of the invention.

Figure 2:
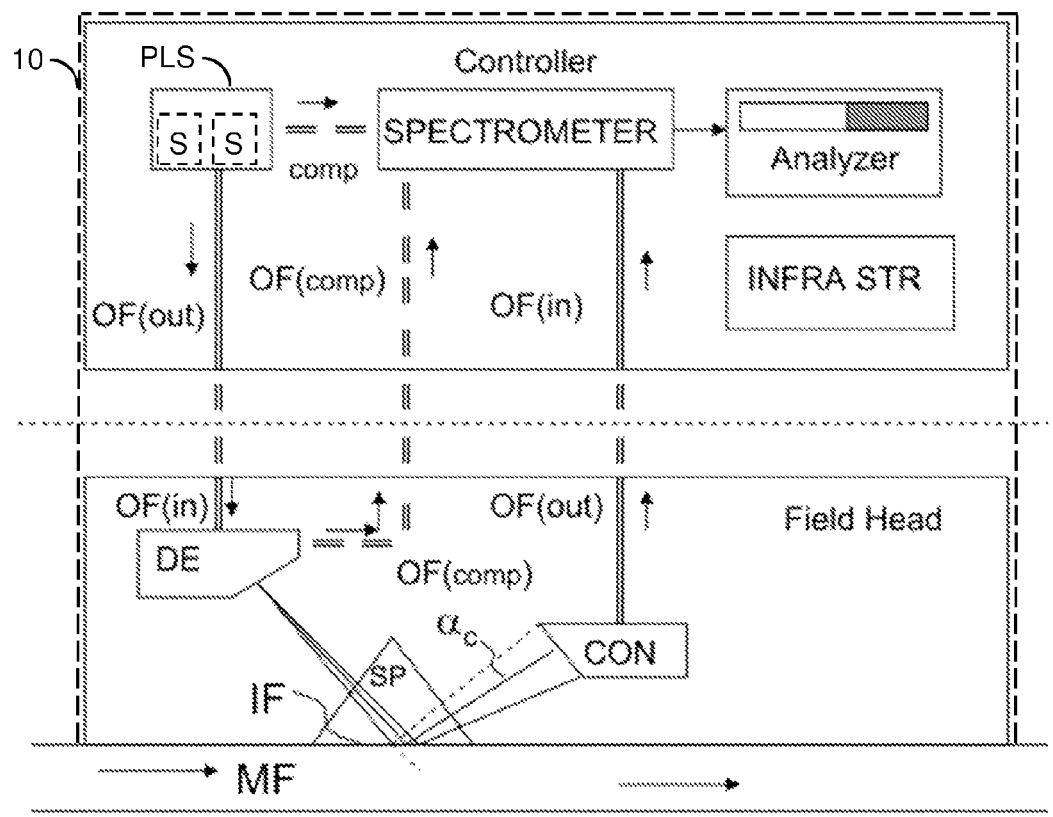

FIG. 2. Schematic illustration of an example of an embodied field head, controller and system according to an embodiment of the invention are shown, and FIG. 3 Illustrates critical angle dependence on concentration and wave length for visible light.

DETAILED DESCRIPTION

FIG. 2 illustrates an optical system comprising at least one field head and at least one controller of a field head according to an embodiment of the invention. The number of field heads and/or controllers in a system is not limited to the mere illustrated, as a skilled man in the art understands from the embodiments of the invention. Although there is a dashed line illustrated in FIG. 2 there between the field head and the controller indicative of remoteness, according to an embodiment they can be assembled into the same cover 10, shown in dashed lines, to comprise a single instrument. In this kind of embodiments, the number of field heads under the same controller's control is not limited, neither the number of remote field head units pluggable to the device, but nor for the internally connected field heads. The wave guide can be used for separating the field head and the controller, for example one in a first room and the other in a second room or space.

FIG. 2 illustrates also a controller according to an embodiment of the invention. Such a controller comprises a polychromatic light source PLS to be used fro providing the light needed in the field head. The light is arranged to be connectable via the OF(out) of the controller to the OF(in) of the field head.

A skilled man in the art knows many ways to implement the PLS, as such, for the embodiments of the invention. The PLS can be a single source, but can comprise optionally several sources S, shown in dashed lines, so that the need for broad band spectrum can be covered in an embodiment and/application specific way from ultraviolet wave lengths to infrared wave lengths. The broad band light can so comprise components from ultraviolet light, visible light and/or infrared light, as a continuum in suitable part, but also according to a variant of an embodiment also in discrete sub bands residing at the wavelength range there between the extremes in ultraviolet short wave length-side and the infrared long wave length side. However, with the provision that the wave guides OF(in, out, comp) do not limit the intensity to be observed beyond utilizability of the used spectrometer.

In some embodiments a compensation signal may be used, in one ensemble of embodiments internally in another internally and/or via field head. The compensation signal can be used to soften, for example, the otherwise bumpy response curve of the spectrometer, wave guides and/or the light source. Controller's internal compensation line from the PLS to spectrometer may be embodied also optionally optically although indication of the OF for wave guide is not shown as such in the figure in that respect for the appropriate embodiments only where such compensation is used.

The controller in FIG. 2 comprises also INFRA STR to demonstrate various infra-structure related things and supports for the electro-mechanical structures for implementation of the controller's components and connections, as well as power feed lines and signal routing and/or interfacing to the outer devices and/or displays etc. The INFRA STR comprises also in an embodiment such memories, microprocessors as well as the software codes and data, databases etc. that are needed for the practical implementation of a particular embodiment for a measurement purpose to measure a refractive index derivable quantity of a medium, i.e. concentration of a substance in the composition comprising the medium in accordance of the embodied embodiments. The infra structure as such is thus described only as a block for simplicity and clarity reasons.

In practice the arrangement of further details and the selected wavelengths to be utilized depend on the medium MF to be used in the flow, or the sample in the still conditions. Although MF illustrates embodiment in a measurement for a fluid, when read and understood the embodiments, a skilled man in the art can put the sensor prism SP in contact also with a solid medium, which can be moving or can be solidly at its place with a zero velocity in respect to the SP. That kind of embodiments may be useful to embody within application directed to a process of films and/or plates or sheets or other lamellae.

In FIG. 2, the field head according to an embodiment of the invention is illustrated to comprise wave guide as the indicated optical fiber (OF) for input (in) and output (out) for the respective incident light from a polychromatic source and for the reflected light to be led to the spectrometer. According to an embodiment of the invention there is also a compensation signal output OF(comp) for utilization in the light source characteristic compensation for the spectrometer.

As in an embodiment of the invention, all the components in the field head are opto-mechanical, there is no electricity needed at all in the field head. This is advantageous when working with flammable and/or explosive medium flows or conditions. Thus, intrinsically safe operation can be gained. Another advantage is that the field head so embodied can tolerate elevated or very low temperatures as there is no heat/coldness sensitive electronics in the field head.

The mechanical wear resistance of the sensor prism and/or its coating in the operation conditions, especially the temperature, defines the operational maximum temperature, provided, that the optical wave guide lines OF(in), OF(out) and OF(comp) when present tolerate that temperature, but also to the other environmental conditions.

The dispersive element DE can be embodied by using a prism and/or a diffractive grating, situated as a distinct component from the measurement prism SP in one ensemble of embodiments, for gaining wider spread of the wave lengths at the ends of the broad band spectrum, but in another ensemble of embodiments DE is integrated with the SP for a compact structure.

The wave guide implemented compensation OF(comp) is an optional feature in an embodiment of the field head and/or controller, and thus illustrated by a dashed line. Dashed line is also used between the wave guide connected controller and field head to demonstrate that these parts can be remote to each other. This is an advantage, when the electronics in the INFRA STR should be kept away from the field head because of the operating conditions, for instance.

The condenser CON can be embodied by a chromatic lens. The condenser collects the arriving component beams into the OF(out) of the filed head to be delivered to the spectrometer, to be analyzed by in an analyzer, which can be assisted by a software code utilizable for the calibration and measurements with the system embodied. The condenser CON can be embodied in suitable part also by a bunch of optical fibers so to lead the CLBs to the spectrometer. This option is useful in spatial quantization of the CLBs with such photo-cells/CCD-elements that need external electricity for their operation to respond to the initiatives of the CLBs so reflecting the changes in the refraction index of the medium to be studied. In such embodiment a single fiber or a sub-ensemble of the bunch can be used for leading the corresponding CLB to the photo-cell. According to an embodiment, instead of a photo-cell CCD-element may be used so that the pixels are arranged for receiving the CLBs, so that the CLBs are quantized by the number of the CCD-pixels arranged for each CLB. Thus, it is possible to provide such a single pixel for a single fiber for the spectrometric analysis of the signal, when the location of the input end at the condenser part is known and the output end of the same fiber at the spectrometer location as well as the relation there between on that which input end and output end correspond each other according to the CLB quantization. In this way the, pixels, as such, used in various embodiments, do not need to be necessarily capable to distinguish colors for their output signals, i.e. recognize the wave-length of the arriving light of the CLB.

According to an embodiment the analysis of the signals of the photo-cells or the CCD element or the parts thereof can be implemented as such according to a known technique in suitable part.

According to an embodiment of the invention the wave guide and/or the field head is shielded by a conductive film for conducting charge built up to ground, such a built up potentially threatening to the process or the operative staff.

In an embodiment of the invention, the light can be pulsed. In such an embodiment, the spectrometer may be not needed anymore, and a simple intensity detection can be used for analyzing the critical angle $\alpha_c$, or other angles that correlate with the wavelengths of the component light beams in question.

According to an embodiment of the invention several wavelengths can be used for the determination of the refractive index. In a calibration corresponding to the measurement situation, the shadow edge can be measured, at which wave length it occurs. Similar way, also other wavelengths can be determined, into which angle they should be reflected from the IF. Thus, in a measurement in a utility site for example, drifting of the instrument can be detected and/or compensated as the spectrometer or another analyzer can compare a multitude of wavelengths and the corresponding light beam component angles to the calibration data and thus compensate appropriately the drifts, if any.

According to an embodiment of the invention the dispersive element can be implemented by a turbine scanner, i.e. with a rotating polygon mirror, whose mirror faces constitute a repeatable scanning movement of the incident light beam and thus over the condenser aperture for the light input to be collected into the waveguide leading to the spectrometer. However, in such embodiments where no electricity can be used, the movement may be arranged by means of the fluid (pressurized air flow for example) and a mechanism that utilizes the fluid movement and turns it to the movement of the turbine scanner, as the scanning speed can be slow, i.e. not to exceed 1000 rps.

Figure 3:
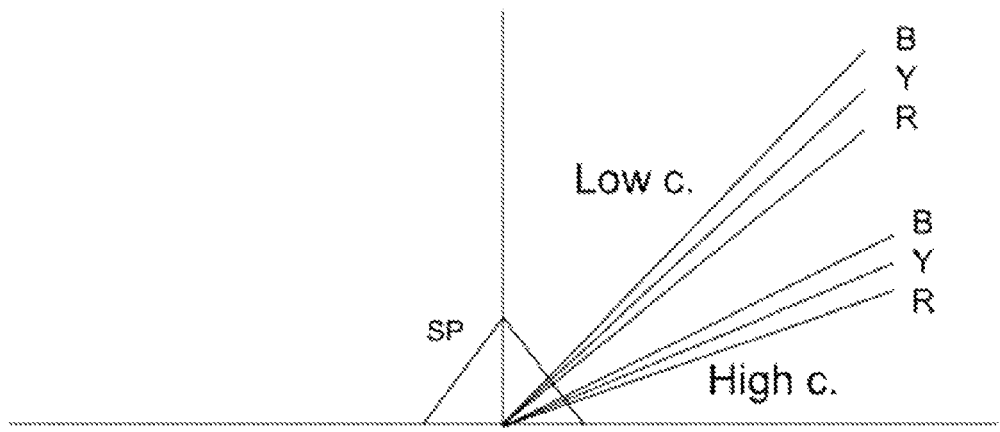

In FIG. 3 in accordance of an embodiment of the invention described in other parts of the application text, Red (R) refers to the long wave length end of the range of applied polychromatic light and Blue (B) refers to the short wave length end of the range of applied polychromatic light, irrespectively on that do the ranges reside totally or in part in ultraviolet, in visible and/or in infrared wavelength range. According to an embodiment, of the invention the direction of the wavelength dispersion and/or spectrometer scan of the wavelengths can be switched, so to increase or suppress the dynamic range of angles of reflected light, that were demonstrated for blue, red, and yellow (Y) light for the propagation directions for a low concentration and a high concentration mediums. The appearance of the rays in FIG. 3 is different from the FIG. 2 because of simplicity reasons for illustration.

According to an embodiment, the spectrometer is arranged to provide information to the analyzer on multiple wavelengths of component light beams. This way a redundant measurement can be verified for statistical analysis. A further advantage is thus achievable for example for detection of anomalies in the medium density, i.e. multiphase presence and/or medium fluctuations originating departures of the refraction index that may be traced and thus associated via the medium flow density, to be used for estimates on turbulence and/or its components.

What is claimed is:

1. A field head of an optical instrument for measuring a refractive index of a medium, or a quantity derivable therefrom, comprising:
    a measurement prism having a boundary surface in contact with the medium;
    a first wave guide for providing broad-band light from a broad band light source;
    a dispersive element for dispersing the broad-band light into at least one component light beam belonging to a plurality of component light beams, so that each incident component light beam in the plurality has a differently directed propagation path and at least one different wave length distinctive relative to others of the plurality of component light beams; and
    a condenser for collecting into a second wave guide at least one component light beam as reflected at the measurement prism boundary surface;
    wherein the dispersive element is arranged to direct at least one component light beam into a critical angle of total reflection from the boundary surface, and at least another component light beam into an angle leading into the condenser arranged to collect at least one of the another component light beams to be passed to a spectrometer.

2. The field head of claim 1, wherein a component light beam of the plurality of light beams is arranged to be incident to the measurement prism boundary surface in an out of focus geometry at the surface.

3. The field head of claim 1, wherein a component light beam of the plurality of light beams is arranged to be incident to the measurement prism boundary surface in a converging geometry to focus on the surface.

4. The field head of claim 1, wherein a component light beam of the plurality of light beams is arranged to be dispersed into a component light beam specific incident angle as a function of wavelength of the broad-band light.

5. The field head of claim 1, further comprising wave guide connectors for guiding light at least into the first wave guide or out of the second wave guide.

6. The field head of claim 1, wherein at least one of the dispersive element and the measurement prism comprises a diffraction grating.

7. The field head of claim 1, wherein the dispersive element and the measurement prism are combined in one component.

8. The field head of claim 1, further comprising a wave guide line output for an optical compensation signal for a controller.

9. The field head of claim 1, further comprising at least one of an antistatic coating configured to avoid charge build-up on the field head and a grounding device configured to lead charge built-up to a ground.

10. The field head of claim 1, further comprising wave guide connectors for control signals for controlling the field head.

11. A controller of a field head of an optical instrument, comprising:
    a light source for providing polychromatic light via a first wave guide for forming a plurality of component light beams to propagate in the field head, the field head being configured according to claim 1; and
    a spectrometer for spectrum analysis of light inputted therein via at least one input wave guide from the field head.

12. The controller of claim 11, wherein the light source is arranged to transmit polychromatic light with a continuous wavelength distribution.

13. The controller of claim 11, wherein the light source comprises a plurality of monochromatic light sources for providing the component light beams.

14. The controller of claim 11, wherein the light source is arranged to provide a compensation signal to the spectrometer for compensation of light source characteristics.

15. The controller of claim 11, wherein the spectrometer has light inputted via a field head.

16. The controller of claim 11, wherein the light source comprises at least one light source that can produce light pulses.

17. The controller of claim 16, wherein the light source comprises at least one of a control device configured to alter a wave length of the light from one pulse to another, and a control device configured to vary a pulse length versus a pulse frequency.

18. An optical system, comprising at least one field head according to claim 1 and at least one controller configured for controlling the at least one field head.

19. The optical system of claim 18, wherein the field head and the controller are integrated into a same cover.

20. A method of determining refractive index via total reflection of a component light beam belonging to a plurality of light beams of broad-band multi-wavelength light, comprising:
    directing at least one component light beam of a first wave length to a medium-boundary surface of a field head prism at a critical angle of total reflection;
    directing at least one other component light beam at a second wave length to the medium-boundary surface to propagate on a path leading to a condenser;
    collecting by the condenser reflected light to a spectrometer arranged for spectrometric analysis of component light beams;
    detecting, based on information on a wave length of at least one component light beam in the plurality of component light beams, a first missing component light beam from a spectrum; and
    computing a refractive index of the medium based on the missing component's wave length.

21. A non-transient computer program product, comprising a computer-readable medium having stored instructions that, when executed by a computer, cause the computer to control a spectrometer according to claim 20.

22. The computer program product of claim 21, wherein the stored instructions cause the computer to implement at least one of a spectrometer controller, a spectrum scanner, a spectrum analyzer, a shoulder defining device, a data-logger, a statistical analyzer, a data-base for storing measurement data, and a graphical device arranged to depict measurement results on a display.

* * * * *